United States Patent [19]

Kühne et al.

[11] 4,100,283
[45] Jul. 11, 1978

[54] GROWTH PROMOTING FEED ADDITIVE OXADIAZINES

[75] Inventors: Manfred Kühne, Pfeffingen; Clemens Kocher, Therwil; Jean Jacques Gallay, Magden, all of Switzerland

[73] Assignee: Ciba-Geigy Corporation, Ardsley, N.Y.

[21] Appl. No.: 780,897

[22] Filed: Mar. 24, 1977

[30] Foreign Application Priority Data

Apr. 1, 1976 [CH] Switzerland .................. 4066/76

[51] Int. Cl.$^2$ ........................................... A61K 31/535
[52] U.S. Cl. ............................. 424/248.5; 424/248.4; 424/248.51; 424/248.52; 424/248.53; 424/248.54; 424/248.56; 424/248.57; 544/68
[58] Field of Search ................ 424/248.4, 248.51; 260/244 R

[56] References Cited

U.S. PATENT DOCUMENTS

| | | | |
|---|---|---|---|
| 3,574,201 | 4/1971 | Breuer | 260/244 R |
| 3,966,721 | 6/1976 | Huff | 260/244 R |
| 4,064,243 | 12/1977 | Huff et al. | 424/248.5 |

Primary Examiner—V. D. Turner

Attorney, Agent, or Firm—Harry Falber

[57] ABSTRACT

Feed additives for promoting the growth of domestic and productive animals, which additives contain as active ingredient at least one compound of the formula I

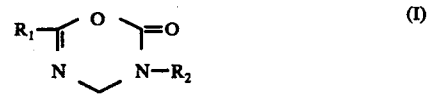

wherein
  $R_1$ represents a 5- or 6-membered, N-, S- or O-containing heterocyclic-aromatic radical, optionally substituted by halogen, lower alkyl, phenyl, nitro, cyano, $(R_3)_2NCO-$, $(R_3)_2N-$, $R_3O-$, $R_3SO_2-$, $R_3SO-$ or $R_3S-$,
  $R_2$ represents lower alkyl, alkenyl or cycloalkyl optionally bound by way of an alkylene bridge, and
  $R_3$ represents lower alkyl, alkenyl or alkoxyalkyl having a total of up to 8 carbon atoms, or quaternary ammonium compounds or N-oxides of the N-containing heterocyclic-aromatic radicals, together with suitable carriers and/or distributing agents.

1 Claim, No Drawings

GROWTH PROMOTING FEED ADDITIVE OXADIAZINES

The present invention relates to feed additives containing diazine compounds having a growth-promoting action for domestic and productive animals, as well as to the use thereof.

The diazine compounds correspond to the following formula

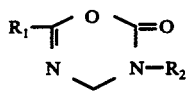
(I)

wherein
$R_1$ represents a heterocyclic-aromatic radical, optionally substituted by halogen, lower alkyl, phenyl, nitro, cyano, $(R_3)_2NCO-$, $(R_3)_2N-$, $R_3O-$, $R_3SO_2-$, $R_3SO-$ or $R_3S-$, $R_2$ represents lower alkyl, alkenyl or cycloalkyl optionally bound by way of an alkylene bridge, and $R_3$ represents lower alkyl, alkenyl or alkoxyalkyl having a total of up to 8 carbon atoms.

By lower alkyl in the formula I are meant straight-chain or branched-chain radicals having 1 to 6 carbon atoms, preferably 1 to 4 carbon atoms, such as methyl, ethyl, n-propyl, isopropyl, n-butyl, isobutyl, sec.-butyl or tert.-butyl, as well as n-pentyl or n-hexyl and isomers thereof. Alkenyl groups contain 2 – 6, preferably 3 – 4 carbon atoms, such as allyl or methallyl. Alkoxyalkyl groups have a total of up to 8 carbon atoms. Cycloalkyl groups contain 3 to 6 carbon atoms and can be bound by way of a methylene or ethylene bridge and can optionally carry methyl or ethyl as substituents. By heterocyclic-aromatic radicals are meant 5- to 6-membered N-, S- or O-containing, optionally benzocondensed ring systems. These are, for example, pyrazinyl, pyrolyl, thiazolyl, imidazolyl, pyrimidinyl, furyl, thienyl, pyridinyl, quinolyl, indolyl and benzofuranyl. There can be present here nitrogen-containing heterocycles in the form of their quaternary ammonium compounds or N-oxides.

The novel diazine derivatives of the formula I are obtained by a process in which an amide of the formula II

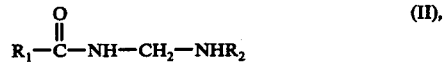
(II), wherein $R_1$ and $R_2$ have the meanings given under the formula I, is cyclised with a compound of the formula III

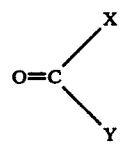
(III)

wherein X or Y independently of one another represent chlorine or the radicals

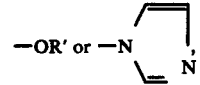

wherein R' represents alkyl having 1 to 2 carbon atoms.

Cyclisation is performed by reacting the amide of the formula II at a temperature of between $-50°$ C and $+30°$ C with a compound of the formula III in the presence of a base in solvents and/or diluents inert to the reactants; and subsequently effecting ring closure in the presence of a base at temperatures of between $-15°$ and $120°$ C, optionally under pressure.

Suitable solvents or diluents are aliphatic or aromatic hydrocarbons such as benzene, toluene, xylenes or hexane; halogenated hydrocarbons such as chloroform or methylene chloride; ketones such as acetone or methyl ethyl ketone; nitriles such as acetonitrile; or dimethylformamide or dimethylsulphone; particularly, however, ethers and ethereal compounds, such as dialkyl ether, dioxane, tetrahydrofuran or 1,2-dimethoxyethane; as well as two-phase mixtures such as water/benzene. Bases to be mentioned are, in particular, tertiary amines such as trialkylamines, pyridine or pyridine bases, also NaH or, in the case of aqueous mixtures, hydroxides and carbonates of alkali metal and alkaline-earth metals.

The amides of the formula II used as starting materials can be produced as follows: An amide of the formula IV

(IV)

is reacted, in the presence of an anhydrous organic or inorganic acid (e.g. HCl) at a temperature of between $-40°$ C and $+30°$ C in an inert organic solvent liquid under the reaction conditions, with a hexahydro-s-triazine of the formula V

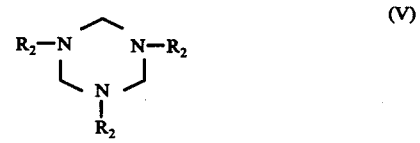
(V)

under aminomethylating conditions. The substituents $R_1$ and $R_2$ have the meanings given under the formula I. The intermediates occurring as salts of the employed acid are converted, by treatment with bases, into the free amides of the formula II.

According to another method, described in Chem. Pharm. Bull. 21, (12), pp. 2775-2778 [1973], compounds of the formula II are also obtainable by simultaneous reaction of compounds of the formula IV with formaldehyde and the amino hydrochloride $R_2-NH_2.HCl$ in aqueous alcohol solution. In this case too the intermediates of the formula II occur as salts (hydrochlorides) and are converted by the addition of bases into the free amides.

As described in Example 3, the compounds of the formula I can be produced advantageously in the single-vessel process directly from the amides of the formula IV by reacting these, in the presence of an anhydrous acid, with a hexahydro-s-triazine of the formula V in an inert organic solvent; and subsequently cyclising the resulting intermediates of the formula II, without isolation, with a compound of the formula III in the presence of a base. This special embodiment of the process for producing compounds of the formula I offers surprisingly the advantage that also those compounds of the formula II wherein $R_1$ represents a heterocycle which is itself sensitive to alkali, or which is rendered so by a substituent, can be cyclised without difficulty.

Compounds of the formula I produced by the described process can if required be converted, provided that they contain a ring nitrogen atom in the radical $R_1$ or a sulphur atom or the SO- group in a substituent of $R_1$, in an additional operation, by means of a suitable oxidising agent, e.g. peroxy acid, into their oxides, such as N-oxides, sulphoxides or sulphones. Furthermore, compounds of the formula I can, provided they contain a quaternisable ring nitrogen atom in the radical $R_1$, be optionally converted by a suitable quaternising agent into their quaternary salts.

The following Examples illustrate the process according to the invention. The temperatures are given in degrees Centigrade.

EXAMPLE 1

A suspension of 50.6 g of N-(methylaminomethyl)-pyrazineamide hydrochloride in 500 ml of water is neutralised at 0° to 25° with 125 ml of 2N sodium hydroxide solution. After extraction with ethyl acetate, the organic phase is dried over magnesium sulphate and the solvent is evaporated off. The residue is taken up in 300 ml of tetrahydrofuran, and there is then added dropwise 24.8 g of phosgene in 300 ml of tetrahydrofuran. The addition is made at 0° to 25° during one hour. There is subsequently added at room temperature, in the course of one further hour, 39.5 g of pyridine dissolved in 100 ml of tetrahydrofuran. The reaction mixture is stirred for two further hours and then refluxed for 3 hours. After cooling, the resulting precipitate is filtered off; the filtrate is concentrated to dryness by evaporation, the residue is taken up in chloroform, washed firstly with sodium bicarbonate solution and then with water and dried. The solvent is evaporated off and the residue is recrystallised from ethylene acetate/hexane to obtain 6-pyrazino-3-methyl-3,4-dihydro-2H-1,3,5-oxadiazin-2-one having a melting point of 151° to 152° C.

EXAMPLE 2

A suspension of 19 g of N-(methylaminomethyl)-picolinamidebis-hydrochloride in 400 ml of ethyl acetate is treated with excess concentrated sodium hydroxide solution with ice cooling, and the free base in the organic phase is rapidly separated, dried and freed from solvent. The free base is dissolved in 120 ml of dimethoxyethane, and the solution is added dropwise at 0° to +5°, within one hour, to a solution of 10 g of phosgene in 120 ml of dimethoxyethane. The temperature is afterwards allowed to rise to 25° and a solution of 7.6 g of pyridine in 120 ml of dimethoxyethane is added dropwise during one hour; stirring is then maintained for 2 hours at room temperature. Any precipitate formed is subsequently filtered off; the filtrate is concentrated by evaporation and the residue is taken up in a mixture of 500 ml of ethyl acetate and 20 ml of water. The water phase is extracted twice with 50 ml of ethyl acetate each time. From the combined ethyl acetate extracts, there is obtained, by concentration by evaporation, a brown oil which can be crystallised by treatment with benzene and hexane. The crystallised product is N'-(chlorocarbonyl)-N'-methylaminomethyl-picolinamide and melts at 89° - 91° C.

For cyclisation there is produced from a commercial NaH dispersion in oil, by washing with benzene and dimethoxyethane, a suspension of 0.78 g of NaH in 40 ml of dimethoxyethane. To this suspension is added dropwise at room temperature, within 20 minutes, 5.4 g of the above-described intermediate (m.p. 89° - 91° C) dissolved in 40 ml of dimethoxyethane. The reaction at the commencement is slightly exothermic. After completion of the dropwise addition, the temperature is slowly raised to +60° C and stirring at this temperature is continued for about 5 hours. The reaction mixture is then allowed to cool, the mixture is poured into a mixture of sodium acetate and ice and extracted with chloroform. The chloroform extract is concentrated by evaporation and the residue is recrystallised from ethyl acetate/hexane. The product is 6-(2-pyridinyl)-3-methyl-3,4-dihydro-2H-1,3,5-oxadiazin-2-one, m.p. 174° - 177° C.

EXAMPLE 3

3.8 g = 0.105 mole of HCl gas is introduced into 150 ml of anhydrous dimethoxyethane. This solution is cooled to −35° C and 4.3 g = 0.033 mole of trimethylhexahydrotriazine is added dropwise. There is afterwards added to the solution, cooled to −30° C, 19.1 g = 0.1 mole of finely powdered and well dried 2,6-dichloronicotinamide. The addition of the amide is made with vigorous stirring. Stirring is continued for a about one further hour at −30° C, and the temperature of the mixture is then allowed to rise overnight to room temperature. The mixture is subsequently again cooled to −35° C, and there are successively added at −35° C 100 ml of anhydrous dimethoxyethane, a solution of 11.9 g = 0.12 mole of phosgene in 60 ml of toluene and a solution of 14.4 ml of anhydrous pyridine in 20 ml of dimethoxyethane, the two last-mentioned being added dropwise with vigorous stirring. Stirring is continued for about one hour at −30° C and the temperature is subsequently allowed to rise to 0° C in the course of about 2 hours. There is afterwards added dropwise a further 26 ml of pyridine = 0.33 mole (with stirring). The temperature is allowed after 1 hour to slowly rise to room temperature and the stirrer is then switched off. The reaction mixture is now heated to reflux temperature and refluxed for 15 hours. It is afterwards allowed to cool; the liquid phase is decanted from the oily precipitate, and the solvent is completely removed. The residue is taken up in a mixture of water and ethyl acetate. The aqueous phase is further extracted twice with ethyl acetate and then discarded. The combined ethyl acetate extracts are concentrated by evaporation. Column chromatography on silica gel then yields therefrom pure 6-(2,6-dichloro-3-pyridinyl)-3-methyl-3,4-dihydro-2H-1,3,5-oxadiazin-2-one having a melting point of 126° - 128° C.

EXAMPLE 4

28.7 g = 0.15 mole of 6-(4'-pyridinyl)-3-methyl-3,4-dihydro-2H-1,3,5-oxadiazin-2-one is dissolved in 150 ml of chloroform; the solution is cooled to 0° C, and there is then added dropwise a solution of 25.8 g of meta-chloroperbenzoic acid in 180 ml of chloroform. After completion of the dropwise addition, the temperature is allowed to rise within 6 hours to 23° C, and stirring is continued overnight for 48 hours at this temperature. After this length of time, the mixture should contain no further peroxy acid. The solvent is then evaporated off and the residue is recrystallised from methanol. The resulting product is 6-(4'-pyridinyl)-3-methyl-3,4-dihydro-2H-1,3,5-oxadiazin-2-one-1'-oxide, which melts at 246° – 247° C.

EXAMPLE 5

2.37 g = 10 millimoles of 6-(6'-methylthio-3'-pyridinyl)-3-methyl-3,4-dihydro-2H-1,3,5-oxadiazin-2-one is dissolved in 200 ml of chloroform and the solution is cooled to 0° C. An addition is then made dropwise, within 4 hours, of 1.72 g = 10 millimoles of meta-chloroperbenzoic acid dissolved in 50 ml of chloroform, and stirring is continued for 4 hours. The temperature is then allowed to rise to 22° C and stirring is maintained for a further 15 hours. After this length of time, no further peroxide should be detectable. The reaction mixture is subsequently concentrated by evaporation and the residue is recrystallised from ethyl acetate to yield 6-(6'-methylsulphinyl)-3'-pyridinyl)-3-methyl-3,4-dihydro-2H-1,3,5-oxadiazin-2-one, m.p. 197° – 199° C.

EXAMPLE 6

1 g of 6-(4'-pyridinyl)-3-methyl-3,4-dihydro-2H-1,3,5-oxadiazin-2-one is dissolved in 12 ml of acetonitrile. To this solution is added 2 g of methyl iodide, and the initially clear solution is allowed to stand overnight at room temperature. The thick slurry formed is filtered under suction and the crystals are well washed with ethyl acetate. The resulting salt melts at 198° – 199° C with decomposition. It is 6-(1'-methyl-4'-pyridinyl-onium)-3-methyl-3,4-dihydro-2H-1,3,5-oxadiazin-2-one-iodide.

The following compounds are produced analogously to those in the preceeding Examples:

$$R_1 - \underset{N}{\overset{O}{\underset{\|}{C}}} - \underset{N-R_2}{\overset{O}{\underset{\|}{C}}} = O$$

| No. | R$_2$ | R$_1$ | Melting point in ° C |
|---|---|---|---|
| 1 | CH$_3$ | 4-pyridinyl | 163–164 |
| 2 | CH$_3$ | 3-pyridinyl | 138–140 |
| 3 | CH$_3$ | 2-pyridinyl | 174–177 |
| 4 | CH$_3$ | 2-thienyl | 204–205 |
| 5 | CH$_3$ | 2-furanyl | 157–158 |
| 6 | CH$_3$ | 2-(5-nitro-furanyl) | 211–213 |
| 7 | CH$_3$ | 2-(5-methyl-thienyl) | 136–137 |
| 8 | CH$_3$ | 2-(1-methyl-pyrrolyl) | 178–181 |
| 9 | CH$_3$ | 2-quinolinyl | 157–159 |
| 10 | CH$_3$ | 3-(2-chloropyridinyl) | 80–82 |
| 11 | CH$_3$ | 3-(6-chloropyridinyl) | 222–224 |
| 12 | CH$_3$ | 4-(2-phenyl-quinolinyl) | 206–208 |
| 13 | CH$_3$ | 5-(2,4-bis-diethylamino-pyrimidinyl) | |
| 14 | CH$_3$ | 6-(2,4-bis-diethylamino-pyrimidinyl) | |
| 15 | CH$_3$ | 2-benzofuranyl | 256–258 |
| 16 | CH$_3$ | 4-pyridinyl-N-oxide | 246–247 |
| 17 | CH$_3$ | 4-(1-methyl-pyridinium-iodide) | 198–199 |
| 18 | CH$_3$ | 3-pyridinyl-N-oxide | 195–199 |
| 19 | CH$_3$ | 3-(1-methyl-pyridinium-iodide) | 194–197 |
| 20 | CH$_3$ | 3-(6-[4-morpholinyl-]-pyridinyl) | 197–200 |
| 21 | CH$_3$ | 4-(2,6-dichloropyridinyl) | 141–143 |
| 22 | CH$_3$ | 3-(2,6-dichloropyridinyl) | 126–128 |
| 23 | CH$_3$ | 3-(6-methylthio-pyridinyl) | 184–187 |
| 24 | CH$_3$ | 3-(5-nitro-6-methylthio-pyridinyl) | 219–220 |
| 25 | CH$_3$ | 2-benzoxazolyl | 251–253 |
| 26 | CH$_3$ | 3-(6-methylsulphonyl-pyridinyl) | 225–227 |
| 27 | CH$_3$ | 3-(6-methylsulphinyl-pyridinyl) | 197–199 |
| 28 | CH$_3$ | 2-(5-nitro-benzofuranyl) | |
| 29 | CH$_3$ | 2-(6-nitro-benzofuranyl) | |
| 30 | CH$_3$ | 4-quinolinyl | 138–140 |
| 31 | CH$_3$ | 5-(2-chloro-4-diethylamino-pyrimidinyl) | |
| 32 | CH$_3$ | 6-(2-chloro-4-diethylamino-pyrimidinyl) | |
| 33 | CH$_3$ | 3-(2,4-dinitro-thienyl) | |
| 34 | CH$_3$ | 4-(2-methyl-5-cyano-6-chloropyridinyl) | |
| 35 | CH$_3$ | 4-(2-ethoxycarbonyl-pyridinyl) | |
| 36 | CH$_3$ | 3-(5-methoxycarbonyl-pyridinyl) | |
| 37 | CH$_3$ | 2-(6-methoxycarbonyl-pyridinyl) | |
| 38 | CH$_3$ | 2-(1-methyl-indolyl) | |
| 39 | CH$_3$ | 2-(3-nitro-thienyl) | |
| 40 | CH$_3$ | 3-(2-nitro-thienyl) | |
| 41 | CH$_3$ | 2-thiazolyl | |
| 42 | CH$_3$ | 5-(1-methyl-4-nitro-imidazolyl) | |
| 43 | CH$_3$ | 5-(2-methyl-6-chlor-pyrimidinyl) | 84–85 |
| 44 | CH$_3$ | 5-(2-methoxy-pyridinyl) | 159–161 |
| 45 | CH$_3$ | 6-(2,4-dimethoxy-pyrimidinyl) | |
| 46 | CH$_3$ | 6-(2,4-dimethoxy-pyridinyl) | |
| 47 | CH$_3$ | 3-(1-methyl-indolyl) | |
| 48 | CH$_3$ | 4-thiazolyl | |
| 49 | CH$_3$ | 4-(2-dimethylaminocarbonyl-pyridinyl) | |
| 50 | CH$_3$ | 5-(2-trifluormethyl-imidazolyl) | |
| 51 | CH$_3$ | 5-(1-methyl-4-cyano-imidazolyl) | |
| 52 | CH$_3$ | 3-(2-methyl-6-chloropyridinyl) | 127–129 |
| 53 | CH$_3$ | 3-(2-methyl-6-methoxy-pyridinyl) | |
| 54 | CH$_3$ | 3-(2-methyl-6-methylthio-pyridinyl) | 125–128 |
| 55 | CH$_3$ | 3-(5-nitro-6-methoxy-pyridinyl) | |
| 56 | CH$_3$ | 3-(5-nitro-6-chloro-pyridinyl) | |
| 57 | CH$_3$ | 3-(5-nitro-6-cyano-pyridinyl) | |
| 58 | CH$_3$ | 3-(6-chloro-2-methylthio-pyridinyl) | |
| 59 | CH$_3$ | 4-(2,3,5,6-tetrachloro-pyridinyl) | |
| 60 | CH$_3$ | 3-(6-dimethylamino-pyridinyl) | 188–190 |
| 61 | CH$_3$ | 3-(6-trimethylammonium-pyridinyl)-chloride | |
| 62 | CH$_3$ | 3-(6-cyano-pyridinyl) | 221 |

-continued

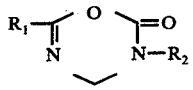

| No. | R₂ | R₁ | Melting point in °C |
|---|---|---|---|
| 63 | CH₃ | 5-(1-benzyl-4-cyano-imidazolyl) | |
| 64 | CH₃ | 2-benzimidazolyl | |
| 65 | CH₃ | 6-(6-bromo-3-pyridinyl) | |
| 66 | CH₃ | 6-(2,6-dibromo-3-pyridinyl) | |
| 67 | CH₃ | 6-(2,4-dimethoxy-5-nitro-pyrimidinyl) | |
| 68 | CH₃ | 3-coumarinyl | |
| 69 | CH₃ | 6-(2,4-bis-dimethylamino-s-triazinyl) | |
| 70 | CH₃ | 6-(2-dimethylamino-4-methoxy-s-triazinyl) | |
| 71 | CH₃ | 4-(2,3,5-trichlor-6-methoxy-pyridinyl) | 167–168 |
| 72 | CH₃ | 2-(3-chloro-6-nitro-benzothienyl) | 234–235 |
| 73 | CH₃ | 2-(3,4-dichlor benzothienyl) | 218–219 |
| 74 | CH₃ | 2-(3-chlorobenzothienyl) | 156–158 |
| 75 | CH₃ | 5-(1,3-dimethyl-4-nitro pyrazolyl) | |
| 76 | CH₃ | 3-(2-methoxy-4-methoxymethyl-5-nitro-pyridinyl) | |
| 77 | CH₃ | 2-(1-methyl-5-nitro-benzimidazolyl) | |
| 78 | CH₃ | 2-(1-methyl-5-nitro-imidazolyl) | |
| 79 | CH₃ | 3-(2-methoxy-4,6-dimethyl-pyridinyl) | |
| 80 | CH₃ | 2-(3-benzoyl-quinoxalyl) | |
| 81 | CH₃ | 2-(3-[3',4'-dimethoxy-benzyl]-quinoxalyl) | |
| 82 | CH₃ | 2-(3-[2',5'-dimethoxy-benzyl]-quinoxalyl) | |
| 83 | CH₃ | 2-(3-[3',4',5'-trimethoxy-benzyl]-quinoxalyl) | |
| 84 | ▷—CH₂ | (3'-[6'-chloro-pyridinyl-]) | 160–163 |
| 85 | ▷—CH₂ | (4'-pyridinyl) | 98–99 |
| 86 | C₂H₅ | (6'-chloro-3'-pyridinyl) | |
| 87 | (CH₃)₂CH | (6'-methoxy-3'-pyridinyl) | |
| 88 | n-C₄H₉ | (2',6'-dichloro-3'-pyridinyl) | |
| 89 | CH₂=CH—CH₂ | (6'-methylthio-3'-pyridinyl) | |
| 90 | CH₃ | 3-(6-fluoro-pyridinyl) | |
| 91 | CH₃ | 3-(2-fluoro-6-chloro-pyridinyl) | |
| 92 | CH₃ | 3-(2-methyl-6-methylsulphinyl-pyridinyl) | 148–149 |
| 93 | CH₃ | 3-(2-methyl-6-methylsulphonyl-pyridinyl) | 214–215 |
| 94 | CH₃ | 3-(6-methyl-pyridinyl) | 180–182 |
| 95 | CH₃ | 3-(6-nitro-pyridinyl) | 223–226 |
| 96 | CH₃ | 4-(2-nitro-pyridinyl) | 130–132 |
| 97 | CH₃ | 3-(6-cyano-2-methylpyridinyl) | |
| 98 | CH₃ | 3-(1-benzyl-pyridinium)-bromide | ~120 (Z) |
| 99 | CH₃ | 4-(1-benzyl-pyridinium)-bromide | 185 (Z) |
| 100 | ▷—CH₂ | 4-(pyridinyl-1-oxide) | 132–134 |
| 101 | CH₃ | 3-(2,6-bis-methylthio-pyridinyl) | 160–162 |
| 102 | CH₃ | 3-[1-(4-nitrobenzyl)-pyridinium]-bromide | 209–211 |
| 103 | CH₃ | 3-[1-(2,6-dichlorobenzyl)-pyridinium]-bromide | 190–200 (Z) |
| 104 | CH₃ | 3-(1-ethyl-pyridinium)-iodide | ~230 (Z) |
| 105 | CH₃ | 2-(3-chloro-7-nitro-benzothienyl) | 225–226 |
| 106 | CH₃ | 3-(6-dimethylamino-pyridinyl-1-oxide) | 143–147 |
| 107 | CH₃ | 4-[1-(2,6-dichlorobenzyl)-pyridinium]-bromide | ca. 185 (Z) |
| 108 | CH₃ | 4-[1-(4-nitrobenzyl)-pyridinium]-bromide | ca. 190 (Z) |
| 109 | CH₃ | 4-(1-ethyl-pyridinium)-iodide | 160–163 (Z) |
| 110 | CH₃ | 4-(2,6-bis-methylthio-pyridinyl) | 137–140 |

The active substances of the formula I have good growth-promoting properties for the rearing and fattening of domestic and productive animals. The active substances are administered, to the animals, both in the solid form and in the liquid form as a solution, emulsion or suspension with the drinking water.

In the feed, the active substances can be applied either in the form of a concentrated premix for mixing with a standard feed, or in the form of a finished feed mixture which is fed directly to the animals.

A suitable premix is, for example, a mixture of an active substance of the formula I with kaolin, lime, aluminium oxide, ground shells, bolus alba, aerosil, starch or lactose.

To produce a feed mixture containing the active ingredient at a concentration of between 1 and 500 ppm, the necessary amounts of premix are thoroughly ground with the appropriate amount of a commercial standard feed for poultry, pigs or ruminants.

Other substances which favourable influence the weight and growth of the animals can be mixed with the feed mixture.

EXAMPLE 7

Promotion of growth of poultry

Groups each of 10 healthy broiler chickens were fed with chicken feed containing 400 ppm of 6-(6'-chloro-3'-pyridinyl)-3-methyl-3,4-dihydro-2H-1,3,5-oxadiazin-2-one.

Groups likewise of 10 healthy broiler chickens of the same breed, which were fed with untreated feed, were used as a comparison.

The increase in weight was determined by daily weighing of the individual chickens, and the intake of feed by weighing the uneaten feed.

After only a few days, the treated chickens, compared with the untreated chickens, showed a clearly greater increase in weight and furthermore a better feed conversion factor.

EXAMPLE 8

Feed concentrates

The following feed mixtures are used to produce in each case 6000 parts by weight of final feed having a content of active ingredient of (a) 25 ppm, (b) 50 ppm, (c) 200 ppm and (d) 400 ppm:

(a) 0.15 part by weight of a compound according to formula I, 49.85 parts by weight of bolus alba, 150.00 parts of a standard feed for poultry;

(b) 0.30 part by weight of a compound according to formula I, 44.70 parts by weight of bolus alba, 5.00 parts by weight of silicic acid, 150.00 parts by weight of a standard feed for poultry;

(c) 1.20 parts by weight of a compound according to formula I, 43.80 parts by weight of bolus alba, 5.00 parts by weight of silicic acid, 150.00 parts by weight of a standard feed for poultry;

(d) 2.40 parts by weight of a compound according to formula I, 47.60 parts by weight of bolus alba, 150.00 parts by weight of a standard feed for poultry.

The active ingredients are either mixed directly with the carriers or absorbed, e.g. dissolved in a suitable solvent, onto the carriers. The resulting material is subsequently ground to the desired particle size of, e.g., 0.5 to 10 microns. These feed premixes are mixed with 5800 parts by weight of standard feed. Furthermore, these feed premixes can be pelletised to give 6000 parts by weight of final feed (feed pellets).

Other growth-promoting and/or biocidal active substances or agents can be mixed with the described compositions according to the invention. Thus, for broadening their sphere of action, the novel compositions can contain, in addition to the stated compounds of the general formula I, for example bactericides, coccidiostatics, bacteriostatics or nematocides.

We claim:

1. A process for promoting the growth of domestic animals and productive livestock which comprises administering to said animals and livestock an effective growth promoting amount of a compound corresponding to the formula

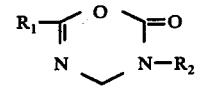

wherein $R_1$ represents a 5- or 6-membered, N-, S- or O-containing heterocyclic-aromatic radical, selected from the group consisting of pyrazinyl, pyrrolyl, thiazolyl, imidazolyl, pyrimidinyl, furyl, thienyl, pyridinyl, quinolinyl, indolyl and benzofuranyl optionally substituted by halogen, lower alkyl, phenyl, nitro, cyano, $(R_3)_2NCO-$, $(R_3)_2N-$, $R_3O-$, $R_3SO_2-$, $R_3SO-$ or $R_3S-$, $R_2$ represents lower alkyl, $C_2-C_6$ alkenyl or $C_3-C_6$ cycloalkyl optionally bound by way of an alkylene bridge, and $R_3$ represents lower alkyl, $C_2-C_6$ alkenyl or alkoxyalkyl having a total of up to 8 carbon atoms, or the quaternary ammonium compounds or N-oxides of the N-containing heterocyclic-aromatic radicals.

* * * * *